US012741999B2

(12) United States Patent
Alsina-Fernandez et al.

(10) Patent No.: US 12,741,999 B2
(45) **Date of Patent: *Sep. 22, 2026**

(54) INCRETIN ANALOGS AND USES THEREOF

(71) Applicant: Eli Lilly and Company, Indianapolis, IN (US)

(72) Inventors: Jorge Alsina-Fernandez, Indianapolis, IN (US); Tamer Coskun, Carmel, IN (US); Lili Guo, Carmel, IN (US); Hongchang Qu, Carmel, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 142 days.

This patent is subject to a terminal disclaimer.

(21) Appl. No.: 18/497,390

(22) Filed: Oct. 30, 2023

(65) Prior Publication Data

US 2024/0190936 A1 Jun. 13, 2024

Related U.S. Application Data

(63) Continuation of application No. 16/769,015, filed as application No. PCT/US2018/065605 on Dec. 14, 2018, now Pat. No. 11,834,486.

(60) Provisional application No. 62/608,644, filed on Dec. 21, 2017.

(51) Int. Cl.
*C07K 14/605* (2006.01)
*A61K 38/00* (2006.01)

(52) U.S. Cl.
CPC ............ *C07K 14/605* (2013.01); *A61K 38/00* (2013.01)

(58) Field of Classification Search
CPC ...... C07K 14/605; A61K 38/00; A61K 38/26; A61P 1/16; A61P 3/04; A61P 3/06; A61P 3/10
See application file for complete search history.

(56) References Cited

FOREIGN PATENT DOCUMENTS

| | | | | |
|---|---|---|---|---|
| WO | 2010108937 A2 | 9/2010 | | |
| WO | 2015067715 A2 | 5/2015 | | |
| WO | WO-2015067716 A1 * | 5/2015 | ................ | A61P 9/10 |
| WO | 2016111971 A1 | 7/2016 | | |
| WO | 2016209707 A1 | 12/2016 | | |

OTHER PUBLICATIONS

Adessi and Soto, Current Medicinal Chemistry, 2002, 9, 963-978 (Year: 2002).*
Gobeil et al., Hypertension. 1999;33:823-829 (Year: 1999).*
Bachem, Peptides in Diabetes, Peptide Trends, Oct. 2017.
Coskun et al. 2018 LY3298176, a novel dual GIP and GLP-1 receptor agonist for the treatment of type 2 diabetes mellitus: From discovery to clinical proof of concept. Mol Metab 18 3-14.
Frias et al. (2018) Efficacy and safety of LY3298176, a novel dual GIP and GLP-1 receptor agonist, in patients with type 2 diabetes: a randomised, placebo-controlled and active comparator-controlled phase 2 trial. The Lancet, 392 (10160), 2180-2193.
Nørregaard et al: (2018) "A novel GIP analogue, ZP4165, enhances glucagon-like peptide-1-induced body weight loss and improves glycaemic control in rodents" Diabetes, Obesity and Metabolism, 20(1), 60-68.
International Search Report issued by the European Patent Office dated Mar. 27, 2019 for International Application No. PCT/US2018/065605.

* cited by examiner

*Primary Examiner* — Joseph Fischer
(74) *Attorney, Agent, or Firm* — Matthew T. Lord

(57) ABSTRACT

Incretin analogs are provided that have activity at each of the GIP, GLP-1 and glucagon receptors. The incretin analogs have structural features resulting in balanced activity and extended duration of action at each of these receptors. Methods also are provided for treating diseases such as diabetes mellitus, dyslipidemia, fatty liver disease, metabolic syndrome, non-alcoholic steatohepatitis and obesity.

23 Claims, No Drawings

Specification includes a Sequence Listing.

INCRETIN ANALOGS AND USES THEREOF

SEQUENCE LISTING

The present application is being filed along with a Sequence Listing in ST.26 XML format. The Sequence Listing is provided as a file titled "X21791A_US_SeqList" created Oct. 30, 2023 and is 45,056 bytes in size. The Sequence Listing information in the ST.26 XML format is incorporated herein by reference in its entirety.

This disclosure relates to incretin analogs having activity at each of a glucose-dependent insulinotropic polypeptide (GIP), glucagon-like peptide-1 (GLP-1) and glucagon receptors. The incretin analogs described herein can have structural features that provide balanced activity and have extended duration of action at each of these receptors. Such incretin analogs may be useful for treating disorders such as type 2 diabetes mellitus (T2DM), dyslipidemia, metabolic syndrome, non-alcoholic fatty liver disease (NAFLD), non-alcoholic steatohepatitis (NASH) and/or obesity.

Over the past several decades, the prevalence of diabetes has continued to rise. T2DM is the most common form of diabetes accounting for about 90% of all diabetes. T2DM is characterized by high blood glucose levels caused by insulin resistance. The current standard of care for T2DM includes diet and exercise, as well as treatment with oral medications and injectable glucose-lowering drugs including incretin-based therapies, such as GLP-1 receptor agonists.

GLP-1 is a 36-amino acid peptide, the major biologically active fragment of which is produced as a 30-amino acid, C-terminal amidated peptide (GLP-17-36; SEQ ID NO:2) that stimulates glucose-dependent insulin secretion and that prevents hyperglycemia in diabetics. A variety of GLP-1 analogs are currently available for treating T2DM, including dulaglutide, exenatide and liraglutide. Many currently marketed GLP-1 receptor agonists, however, are dose-limited by gastrointestinal side effects, such as nausea and vomiting. When treatment with oral medications and incretin-based therapies are insufficient, treatment with insulin is considered. Despite the treatment options available, significant numbers of individuals receiving approved therapies are not reaching glycemic control goals (see, e.g., Casagrande et al. (2013) *Diabetes Care* 36:2271-2279).

Uncontrolled diabetes can lead to one or more conditions that impact morbidity and mortality of such individuals. One of the main risk factors for T2DM is obesity, and a majority of individuals with T2DM (~90%) are overweight or obese. It is documented that a decrease in body adiposity will lead to improvement in obesity-associated co-morbidities including hyperglycemia and cardiovascular events. Therefore, therapies effective in glucose control and weight reduction are needed for better disease management.

In view thereof, new therapies being studied include compounds having not only activity at a GLP-1 receptor but also activity at one or more other receptors, such as the GIP and/or glucagon receptors. In fact, certain compounds have been described as having triple agonist activity (i.e., activity at each of the glucagon, GLP-1 and GIP receptors). For example, Int'l Patent Application Publication No. WO 2015/067716 describes glucagon analogs having triple agonist activity. Similarly, Int'l Patent Application No. WO 2016/198624 describes analogs of exendin-4, itself a GLP-1 analog, having triple agonist activity. Likewise, Int'l Patent Application Nos. WO 2014/049610 and WO 2017/116204 each describe a variety of analogs having triple agonist activity. Moreover, Int'l Patent Application No. WO 2017/153375 describes glucagon and GLP-1 co-agonists that also are stated to have GIP activity.

Nevertheless, a need remains for treatments, especially T2DM, that are capable of providing effective glucose control, with weight loss benefits and a favorable side effect profile. There also is a need for therapeutic agents available for use with sufficiently extended duration of action to allow for dosing as infrequently as once a day, thrice-weekly, twice-weekly or once a week.

The incretin analogs described herein seek to meet the needs above. Accordingly, this disclosure describes incretin analogs with activity at each of the GIP, GLP-1 and glucagon receptors. Advantageously, the incretin analogs described herein have balanced activity allowing for administration of doses that provide sufficient activity at each receptor to provide the benefits of agonism of that receptor while avoiding unwanted side effects associated with too much activity. Moreover, the incretin analogs described herein have extended duration of action at each of the GIP, GLP-1 and glucagon receptors allowing for dosing as infrequently as once-a-day, thrice-weekly, twice-weekly or once-a-week. In this manner, the incretin analogs result in enhanced glucose control, metabolic benefits such as body weight lowering and/or improved body composition, lipid benefits such as proprotein convertase subtilisin/kexin type 9 (PCSK9) lowering, and/or other benefits such as an increase in bone mass or bone formation or a decrease in bone resorption. This disclosure also describes effective treatments for other disorders or conditions, including obesity, NAFLD, NASH, dyslipidemia, and/or metabolic disorder.

In one embodiment, an incretin analog is provided that includes the formula:

$YX_2X_3GTX_6TSDYSIX_{13}LDKX_{17}AQX_{20}AFIEYLLE$-$GGPSSGAPPPS$, where $X_2$ is Aib, $X_3$ is Q or H, $X_6$ is αMeF or αMeF(2F), $X_{13}$ is L or αMeL, $X_{17}$ is any amino acid with a functional group available for conjugation, where the functional group is conjugated to a $C_{16}$-$C_{22}$ fatty acid, $X_{20}$ is Aib, Q or H (SEQ ID NO:5), and the C-terminal amino acid is optionally amidated, or a pharmaceutically acceptable salt thereof.

In another embodiment, a method is provided for treating a disease such as dyslipidemia, fatty liver disease, metabolic syndrome, NASH, obesity and T2DM. Such methods can include at least a step of administering to an individual in need thereof an effective amount of an incretin analog described herein. In some instances, the disease is fatty liver disease, obesity, NASH or T2DM.

In another embodiment, an incretin analog as described herein is provided for use in therapy. For example, an incretin analog as described herein is provided for use in treating a disease such as dyslipidemia, fatty liver disease, metabolic syndrome, NASH, obesity and T2DM. In some instances, the disease is fatty liver disease, obesity, NASH or T2DM.

In another embodiment, an incretin analog as described herein is provided for use in manufacturing a medicament for treating dyslipidemia, fatty liver disease, metabolic syndrome, NASH, obesity and T2DM. In some instances, the disease is fatty liver disease, obesity, NASH or T2DM.

In another embodiment, a pharmaceutical composition is provided that includes an incretin analog as described herein and a pharmaceutically acceptable carrier, diluent or excipient.

Unless defined otherwise, all technical and scientific terms used herein have the same meaning as commonly understood by one of skill in the art to which the disclosure pertains. Although any methods and materials similar to or equivalent to those described herein can be used in the practice or testing of the incretin analogs, pharmaceutical compositions, and methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

GIP is a 42-amino acid peptide (SEQ ID NO:4) and is an incretin, which plays a physiological role in glucose homeostasis by stimulating insulin secretion from pancreatic beta cells in the presence of glucose.

GLP-1 is a 36-amino acid peptide (SEQ ID NO:2) and also is an incretin, which stimulates glucose-dependent insulin secretion and which has been shown to prevent hyperglycemia in diabetics.

Glucagon is a 29-amino acid peptide (SEQ ID NO:1) that helps maintain blood glucose by binding to and activating glucagon receptors on hepatocytes, causing the liver to release glucose—stored in the form of glycogen—through a process called glycogenolysis.

Oxyntomodulin (OXM) is a 37-amino acid peptide including not only the 29-amino acid sequence of glucagon but also an octapeptide carboxy terminal extension (SEQ ID NO:3) that activates both the glucagon and GLP-1 receptors, with a slightly higher potency for the glucagon receptor over the GLP-1 receptor.

In addition to T2DM, incretins and analogs thereof having activity at one or more of the GIP, GLP-1 and/or glucagon receptors have been described as having a potential for therapeutic value in a number of other conditions, diseases or disorders, including, for example, obesity, NAFLD and NASH, dyslipidemia, metabolic syndrome, bone-related disorders, Alzheimer's disease and Parkinson's disease. See, e.g., Jall et al. (2017) *Mol. Metab.* 6:440-446; Carbone et al. (2016) *J. Gastroenterol. Hepatol.* 31:23-31; Finan et al. (2016) *Trends Mol. Med.* 22:359-376; Choi et al. (2017) *Potent body weight loss and efficacy in a NASH animal model by a novel long-acting GLP-1/Glucagon/GIP triple-agonist (HM15211)*, ADA Poster 1139-P; Ding (2008) *J. Bone Miner. Res.* 23:536-543; Tai et al. (2018) *Brain Res.* 1678:64-74; Müller et al. (2017) *Physiol. Rev.* 97:721-766; Finan et al. (2013) *Sci. Transl. Med.* 5:209; Hölscher (2014) *Biochem. Soc. Trans.* 42:593-600.

As used herein, "about" means within a statistically meaningful range of a value or values such as, for example, a stated concentration, length, molecular weight, pH, sequence identity, time frame, temperature or volume. Such a value or range can be within an order of magnitude typically within 20%, more typically within 10%, and even more typically within 5% of a given value or range. The allowable variation encompassed by "about" will depend upon the particular system under study, and can be readily appreciated by one of skill in the art.

As used herein, and in reference to one or more of the GIP, GLP-1 or glucagon receptors, "activity," "activate," "activating" and the like means a capacity of a compound, such as the incretin analogs described herein, to bind to and induce a response at the receptor(s), as measured using assays known in the art, such as the in vitro assays described below.

As used herein, "amino acid with a functional group available for conjugation" means any natural or unnatural amino acid with a functional group that may be conjugated to fatty acid by way of, for example, a linker. Examples of such functional groups include, but are not limited to, alkynyl, alkenyl, amino, azido, bromo, carboxyl, chloro, iodo, and thiol groups. Examples of natural amino acids including such functional groups include K (amino), C (thiol), E (carboxyl) and D (carboxyl).

As used herein, "$C_{16}$-$C_{22}$ fatty acid" means a carboxylic acid having between 16 and 22 carbon atoms. The $C_{16}$-$C_{22}$ fatty acid suitable for use herein can be a saturated monoacid or a saturated diacid. As used herein, "saturated" means the fatty acid contains no carbon-carbon double or triple bonds.

As used herein, "effective amount" means an amount, concentration or dose of one or more incretin analogs described herein, or a pharmaceutically acceptable salt thereof which, upon single or multiple dose administration to an individual in need thereof, provides a desired effect in such an individual under diagnosis or treatment. An effective amount can be readily determined by one of skill in the art through the use of known techniques and by observing results obtained under analogous circumstances. In determining the effective amount for an individual, a number of factors are considered including, but not limited to, the species of mammal; its size, age and general health; the specific disease or disorder involved; the degree of or involvement of or the severity of the disease or disorder; the response of the individual patient; the particular incretin analog administered; the mode of administration; the bioavailability characteristics of the preparation administered; the dose regimen selected; the use of concomitant medication; and other relevant circumstances.

As used herein, "extended duration of action" means that binding affinity and activity for an incretin analog continues for a period of time greater than native human GIP, GLP-1 and glucagon peptides, allowing for dosing at least as infrequently as once daily or even thrice-weekly, twice-weekly or once-weekly. The time action profile of the incretin analog may be measured using known pharmacokinetic test methods such as those utilized in the examples below.

As used herein, "incretin analog" means a compound having structural similarities with, but multiple differences from, each of GIP, GLP-1 and glucagon, especially human GIP (SEQ ID NO:4), GLP-1 (SEQ ID NO:2) and glucagon (SEQ ID NO:1). The incretin analogs described herein include amino acid sequences resulting in the compounds having affinity for and activity at each of the GIP, GLP-1 and glucagon receptors (i.e., triple agonist activity).

As used herein, "individual in need thereof" means a mammal, such as a human, with a condition, disease, disorder or symptom requiring treatment or therapy, including for example, those listed herein.

As used herein, "treat," "treating," "to treat" and the like mean restraining, slowing, stopping or reversing the progression or severity of an existing condition, disease, disorder or symptom.

As used herein, and with reference to an incretin analog, "triple agonist activity" means an incretin analog with activity at each of the GIP, GLP-1 and glucagon receptors, especially an analog having a balanced and sufficient activity at each receptor to provide the benefits of agonism of that receptor while avoiding unwanted side effects associated with too much activity. Moreover, the incretin analogs having triple agonist activity have extended duration of action at each of the GIP, GLP-1 and glucagon receptors, which advantageously allows for dosing as infrequently as once a day, thrice-weekly, twice-weekly or once a week.

As used herein, "treating" or "to treat" mean restraining, slowing, stopping or reversing the progression or severity of an existing condition, disease, disorder or symptom.

As used herein, and with reference to an incretin analog, "triple agonist activity" means an incretin analog with activity at each of the glucagon, GIP and GLP-1 receptors, especially an analog having a balanced and sufficient activity at each receptor to provide the benefits of agonism of that receptor while avoiding unwanted side effects associated with too much activity. Moreover, the incretin analogs having triple agonist activity have extended duration of action at each of the glucagon, GIP and GLP-1 receptors, which advantageously allows for dosing as infrequently as once-a-day, thrice-weekly, twice-weekly or once-a-week.

The structural features of the incretin analogs described herein result in analogs having sufficient activity at each of the GIP, GLP-1 and glucagon receptors to obtain the favorable effects of activity at each receptor (i.e., triple agonist activity), but not so much activity at any one receptor to either overwhelm the activity at either of the two receptors or result in undesirable side effects when administered at a dose sufficient to result in activity at all three receptors. Non-limiting examples of such structural features in certain embodiments, and with reference to SEQ ID NO:5, include αMeF or αMeF(2F) at position 6, which was found to contribute to optimal glucagon activity, L or αMeL at position 13, which was found to contribute to optimal glucagon and GIP activity; Aib at position 20, which was found to contribute to optimal GIP activity; acylation at position 17, which was found to contribute to optimal glucagon activity; and Y at position 25, which was found to contribute to optimal glucagon and/or GIP activity. Other examples of such structural features include the amino acids described herein at positions 22, 24 and 28-39, which were found to contribute to optimal binding and potency at all three receptors.

The structural features of the incretin analogs described herein also result in analogs having many other beneficial attributes relevant to their developability as therapeutic treatments, including improving the solubility of the analogs in aqueous solutions, improving chemical and physical formulation stability, extending the pharmacokinetic profile, and minimizing potential for immunogenicity. Non-limiting examples of particular structural features that result in such attributes include acylation at position 17 with a $C_{20}$ fatty acid, which contributes to optimal pharmacokinetic (PK) profiles and developability; Aib or H at position 20, which contributes to optimal PK profiles and developability; and the amino acids described herein at positions 22, 24 and 28-39, which contribute to optimal PK, immunogenicity, developability and stability.

It should be noted that the foregoing lists of structural features are exemplary, and not comprehensive, and that the combination of beneficial characteristics of exemplary analogs described herein is not the result of any modification in isolation, but is instead achieved through the novel combinations of the structural features described herein. In addition, the above-described effects of the foregoing lists of modifications are not exclusive, as many of these modifications also have other effects important to the characteristics of the compounds described herein, as described below.

The amino acid sequences of incretin analogs described herein incorporate naturally occurring amino acids, typically depicted herein using standard one letter codes (e.g., L=leucine), as well as alpha-methyl substituted residues of natural amino acids (e.g., α-methyl leucine (αMeL), α-methyl lysine (αMeK), α-methyl phenylalanine (αMeF), and α-methyl 2-fluoropheynylalanine (αMeF(2F)), and certain other unnatural amino acids, such as alpha amino isobutyric acid (Aib). The structures of these amino acids are depicted below:

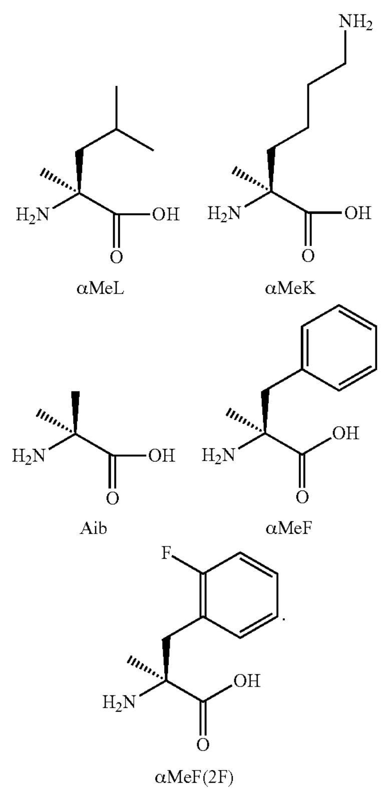

αMeL αMeK

Aib αMeF

αMeF(2F)

As noted above, the incretin analogs described herein have structural similarities to, but many structural differences, from any of the native human peptides. For example, when compared to native human GIP (SEQ ID NO:4), the incretin analogs described herein include modifications at one or more of positions 2, 3, 6, 7, 13, 14, 17, 18-21, 23-25, 28-29 and 30-42. In some instances, the incretin analogs described herein include modifications to the amino acids of native human GIP (SEQ ID NO:4) at each of positions 2, 3, 6, 7, 13, 14, 17, 18, 21, 23-25, 29 and 30-42. In certain instances, the incretin analogs described herein include the following amino acid modifications: Aib at position 2; Q or H at position 3; αMeF or αMeF(2F) at position 6; T at position 7; L or αMeL at position 13; L at position 14; a modified K residue at position 17 which is modified through conjugation to the epsilon-amino group of the K-side chain with a $C_{16}$ to $C_{22}$ fatty acid, optionally through the use of a linker; A at position 18; Q at position 19; Aib, Q or H at position 20; A at position 21; I at position 23; E at position 24; Y at position 25; E at position 28; G at position 29; and replacement of the amino acids at positions 30-42 with the following amino acid sequence: GPSSGAPPPS (SEQ ID NO:12) (and truncated analogs of the tail). In yet other instances, the incretin analogs described herein are amidated. In addition to the modifications described herein, the incretin analogs described herein may include one or more additional amino acid modifications, provided, however, that the analogs remain capable of binding to and activating each of the GIP, GLP-1 and glucagon receptors.

As noted above, the incretin analogs described herein include a fatty acid moiety conjugated, for example, by way of a linker to a natural or unnatural amino acid with a functional group available for conjugation. Such a conjugation is sometimes referred to as acylation. In certain instances, the amino acid with a functional group available for conjugation can be K, C, E and D. In particular instances, the amino acid with a functional group available for conjugation is K, where the conjugation is to the epsilon-amino group of the K side-chain.

The acylation of the incretin analogs described herein is at position 17 in SEQ ID NO:5, which was determined to be the optimal location for inclusion of this structure. The fatty acid, and in certain embodiments the linker, act as albumin binders, and provide the potential to generate long-acting compounds.

The incretin analogs described herein utilize a $C_{16}$-$C_{22}$ fatty acid chemically conjugated to the functional group of an amino acid either by a direct bond or by a linker. The length and composition of the fatty acid impacts the half-life of incretin analogs, their potency in in vivo animal models and their solubility and stability. Conjugation to a $C_{16}$-$C_{22}$ saturated fatty monoacid or diacid results in incretin analogs that exhibit desirable half-life, desirable potency in in vivo animal models, and desirable solubility and stability characteristics.

Examples of saturated $C_{16}$-$C_{22}$ fatty acids for use herein include, but are not limited to, palmitic acid (hexadecanoic acid) ($C_{16}$ monoacid), hexadecanedioic acid ($C_{16}$ diacid), margaric acid (heptadecanoic acid)($C_{17}$ monoacid), heptadecanedioic acid ($C_{17}$ diacid), stearic acid ($C_{18}$ monoacid), octadecanedioic acid ($C_{18}$ diacid), nonadecylic acid (nonadecanoic acid)($C_{19}$ monoacid), nonadecanedioic acid ($C_{19}$ diacid), arachadic acid (eicosanoic acid)($C_{20}$ monoacid), eicosanedioic acid ($C_{20}$ diacid), heneicosylic acid (heneicosanoic acid)($C_{21}$ monoacid), heneicosanedioic acid ($C_{21}$ diacid), behenic acid (docosanoic acid)($C_{22}$ monoacid), docosanedioic acid ($C_{22}$ diacid), including branched and substituted derivatives thereof.

In certain instances, the $C_{16}$-$C_{22}$ fatty acid can be a saturated $C_{18}$ monoacid, a saturated $C_{18}$ diacid, a saturated $C_{19}$ monoacid, a saturated $C_{19}$ diacid, a saturated $C_{20}$ monoacid, a saturated $C_{20}$ diacid, and branched and substituted derivatives thereof. In more particular instances, the $C_{16}$-$C_{22}$ fatty acid can be stearic acid, arachadic acid or eicosanedioic acid, especially arachadic acid.

In some instances, the linker can have from one to four amino acids, an amino polyethylene glycol carboxylate, or mixtures thereof. In certain instances, the amino polyethylene glycol carboxylate has the following structure:

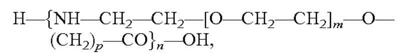

$H—\{NH—CH_2—CH_2—[O—CH_2—CH_2]_m—O—(CH_2)_p—CO\}_n—OH,$ where m is any integer from 1 to 12, n is any integer from 1 to 12, and p is 1 or 2.

In certain instances, the linker can have one or more (2-[2-(2-amino-ethoxy)-ethoxy]-acetyl) moieties, optionally in combination with one to four amino acids.

In instances in which the linker includes at least one amino acid, the amino acid can be one to four Glu or γGlu amino acid residues. In some instances, the linker can include one or two Glu or γGlu amino acid residues, including the D-forms thereof. For example, the linker can include either one or two γGlu amino acid residues. Alternatively, the linker can include one to four amino acid residues (such as, for example, Glu or γGlu amino acids) used in combination with up to thirty-six (2-[2-(2-amino-ethoxy)-ethoxy]-acetyl) moieties. Specifically, the linker can be combinations of one to four E or γE amino acids and one to four (2-[2-(2-amino-ethoxy)-ethoxy]-acetyl) moieties. In other instances, the linker can be combinations of one or two γGlu amino acids and one or two (2-[2-(2-amino-ethoxy)-ethoxy]-acetyl) moieties.

In a specific instance, the incretin analogs described herein have linker and fatty acid components having the structure of the following formula:

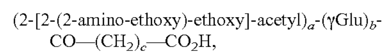

$(2\text{-}[2\text{-}(2\text{-amino-ethoxy})\text{-ethoxy}]\text{-acetyl})_a\text{-}(\gamma Glu)_b\text{-}CO—(CH_2)_c—CO_2H,$ where a is 0, 1 or 2, b is 1 or 2, and c is 16 or 18. In a particular instance, a is 2, b is 1, and c is 18, the structure of which is depicted below:

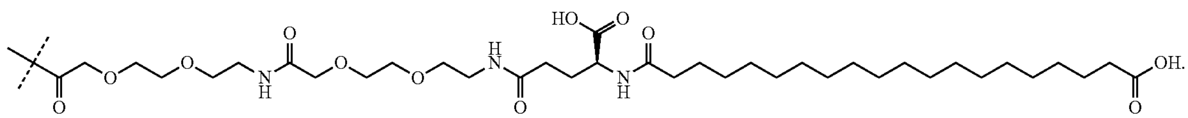

In another specific instance, a is 1, b is 2, and c is 18, the structure of which is depicted below:

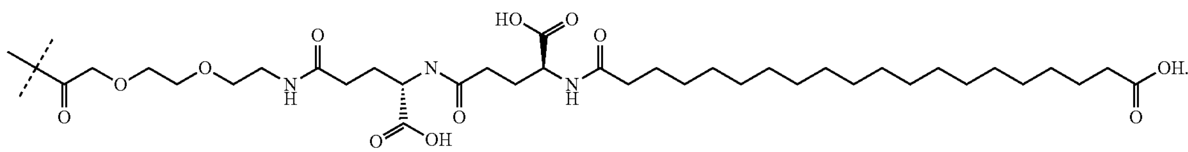

In another specific instance, a is 0, b is 2 and c is 18, the structure of which is depicted below:

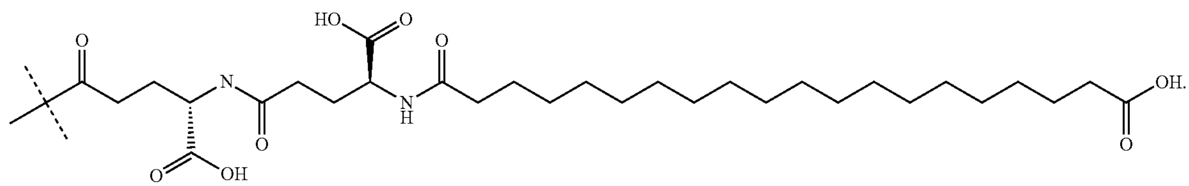

In another specific instance, a is 1, b is 1, and c is 18, the structure of which is depicted below:

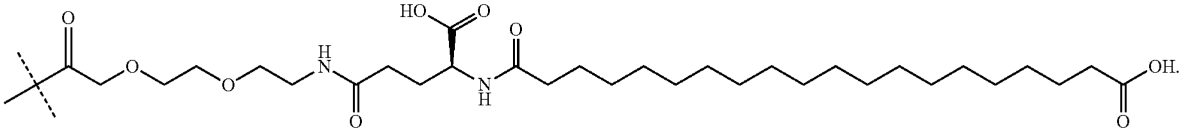

As shown in the chemical structures of Examples 1-6 below, the linker-fatty acid moieties described above can be linked to the epsilon (ε)-amino group of the lysine (K) side-chain.

The affinity of the incretin analogs described herein for each of the GIP, GLP-1 and glucagon receptors may be measured using techniques known in the art for measuring receptor binding levels, including, for example, those described in the examples below, and is commonly expressed as an inhibitory constant (Ki) value. The activity of the incretin analogs described herein at each of the receptors also may be measured using techniques known in the art, including, for example, the in vitro activity assays described below, and is commonly expressed as an effective concentration 50 ($EC_{50}$) value, which is the concentration of compound causing half-maximal simulation in a dose response curve.

The incretin analogs described herein can be formulated as pharmaceutical compositions, which can be administered by parenteral routes (e.g., subcutaneous, intravenous, intraperitoneal, intramuscular or transdermal). Such pharmaceutical compositions and techniques for preparing the same are well known in the art. See, e.g., Remington: The Science and Practice of Pharmacy (Troy, Ed., 21$^{st}$ Edition, Lippincott, Williams & Wilkins, 2006). In particular instances, the incretin analogs are administered subcutaneous.

The incretin analogs described herein may react with any of a number of inorganic and organic acids/bases to form pharmaceutically acceptable acid/base addition salts. Pharmaceutically acceptable salts and common techniques for preparing them are well known in the art (see, e.g., Stahl, et al. Handbook of Pharmaceutical Salts: Properties, Selection and Use, 2$^{nd}$ Revised Edition (Wiley-VCH, 2011)). Pharmaceutically acceptable salts for use herein include sodium, trifluoroacetate, hydrochloride, and acetate salts.

The disclosure also provides and therefore encompasses novel intermediates and methods of synthesizing the incretin analogs described herein, or a pharmaceutically acceptable salt thereof. The intermediates and incretin analogs described herein can be prepared by a variety of techniques known in the art. For example, a method using chemical synthesis is illustrated in the Examples below. The specific synthetic steps for each of the routes described may be combined in different ways to prepare incretin analogs described herein. The reagents and starting materials are readily available to one of skill in the art.

Certain incretin analogs described herein are generally effective over a wide dosage range. For example, dosages for once-weekly administration may fall within a range of about 0.01 to about 30 mg/person/week, within a range of about 0.1 to about 10 mg/person/week or even within a range of about 0.1 to about 3 mg/person/week. Thus, the incretin analogs described herein may be dosed daily, thrice-weekly, twice-weekly or once-weekly, especially once-weekly administration.

The incretin analogs described herein may be used for treating a variety of conditions, disorders, diseases or symptoms. In particular, methods are provided for treating T2DM in an individual, where such methods include at least a step of administering to an individual in need of such treatment an effective amount of an incretin analog described herein, or a pharmaceutically acceptable salt thereof.

Additionally, methods are provided for treating obesity in an individual, where such methods include at least a step of administering to an individual in need of such treatment an effective amount of an incretin analog described herein, or a pharmaceutically acceptable salt thereof.

Additionally, methods are provided for inducing non-therapeutic weight loss in an individual, where such methods include at least a step of administering to an individual in need of such treatment an effective amount of an incretin analog described herein, or a pharmaceutically acceptable salt thereof.

Additionally, methods are provided for treating metabolic syndrome in an individual, where such methods include at least a step of administering to an individual in need of such treatment an effective amount of an incretin analog described herein, or a pharmaceutically acceptable salt thereof.

Additionally, methods are provided for treating NASH in an individual, where such methods include at least a step of administering to an individual in need of such treatment an effective amount of an incretin analog described herein, or a pharmaceutically acceptable salt thereof.

Additionally, methods are provided for treating FLD in an individual, where such methods include at least a step of administering to a subject in need of such treatment an effective amount of an incretin analog described herein, or a pharmaceutically acceptable salt thereof.

In these methods, effectiveness of the incretin analogs can be assessed by, for example, observing a significant reduction in blood glucose, observing a significant increase in insulin, observing a significant reduction in HbA1c and/or observing a significant reduction in body weight.

Alternatively, the incretin analogs described herein or pharmaceutically acceptable salts thereof may be used for improving bone strength in an individual in need thereof. In some instances, the individual in need thereof has hypo-ostosis or hypo-osteoidosis, or is healing from bone fracture, orthotic procedure, prosthetics implant, dental implant, and/or spinal fusion. The incretin analogs described herein also may be used for treating other disorders such as Parkinson's disease or Alzheimer's disease.

Peptide Synthesis

EXAMPLE 1

Example 1 is a compound represented by the following description:

(SEQ ID NO: 6)

Y-Aib-QGT-αMeF-TSDYSILLDKK((2-[2-(2-amino-ethoxy)-ethoxy]-acetyl)$_2$-(γGlu)-CO—$(CH_2)_{18}$—$CO_2H$)AQ-Aib-AFIEYLLEGGPSSGAPPPS-$NH_2$.

Below is a depiction of the structure of Example 1 (SEQ ID NO:6) using the standard single letter amino acid codes with the exception of residues Aib2, αMeF6, K17 and Aib20, where the structures of these amino acid residues have been expanded:

(SEQ ID NO: 6)

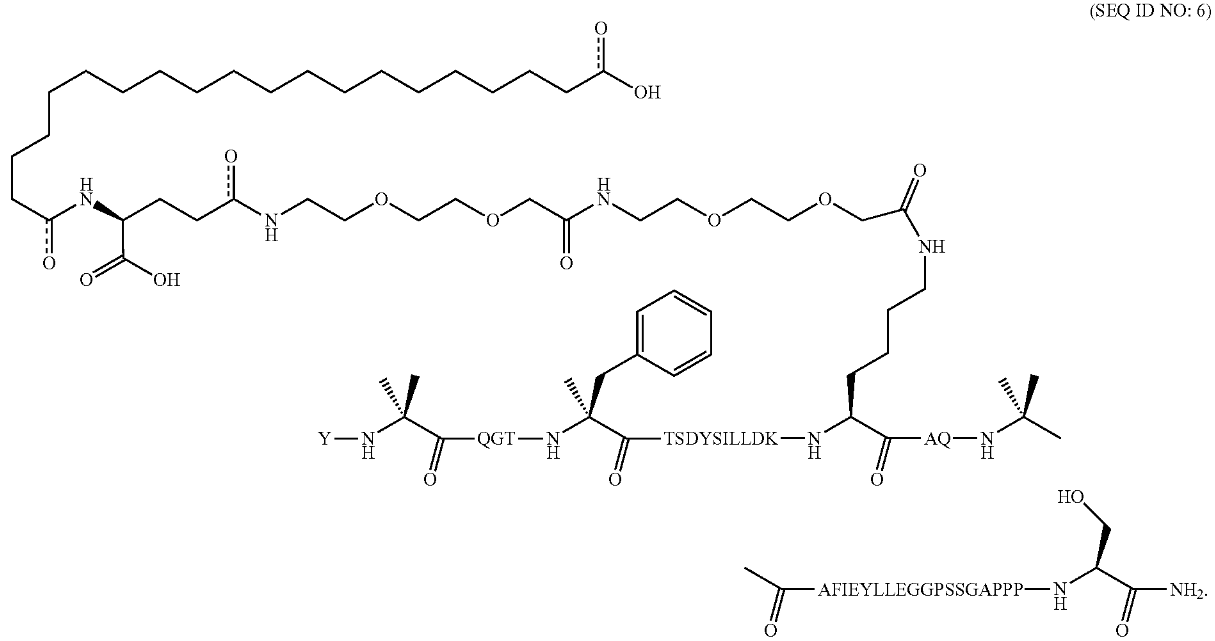

The peptide backbone of Example 1 is synthesized using Fluorenyimethyloxycarbonyl (Fmoc)/tert-Butyl (t-Bu) chemistry on a Symphony X Peptide Synthesizer (Protein Technologies, Inc. Tucson, AZ).

The resin consists of 1% DVB cross-linked polystyrene (Fmoc-Rink-MBHA Low Loading Resin, 100-200 mesh, EMD Millipore) at a substitution of 0.3-0.4 meq/g. Standard side-chain protecting groups are used. Fmoc-Lys(Mtt)-OH) is used for the lysine at position 17, and Boc-Tyr(tBu)-OH) is used for the tyrosine at position 1. Fmoc groups are removed prior to each coupling step (2×7 minutes) using 20% piperidine in DMF. All standard amino acid couplings are performed for 1 hour to a primary amine and 3 hour to a secondary amine, using an equal molar ratio of Fmoc amino acid (0.3M), diisopropylcarbodiimide (0.9M) and Oxyma (0.9M), at a 9-fold molar excess over the theoretical peptide loading. Exceptions are couplings to Ca-methylated amino acids, which are coupled for 3 hours. After completion of the synthesis of the peptide backbone, the resin is thoroughly washed with DCM for 6 times to remove residual DMF. The Mtt protecting group on the lysine at position 17 is selectively removed from the peptide resin using two treatments of 30% hexafluoroisopropanol (Oakwood Chemicals) in DCM (2×40-minute treatment).

Subsequent attachment of the fatty acid-linker moiety is accomplished by coupling of 2-[2-(2-Fmoc-amino-ethoxy)-ethoxy]-acetic acid (Fmoc-AEEA-OH, ChemPep, Inc.), Fmoc-glutamic acid α-t-butyl ester (Fmoc-Glu-OtBu, Ark Pharm, Inc.), mono-OtBu-eicosanedioic acid (WuXi AppTec, Shanghai, China). 3-Fold excess of reagents (AA:PyAOP:DIPEA=1:1:1 mol/mol) are used for each coupling that is 1-hour long.

After the synthesis is complete, the peptide resin is washed with DCM, and then thoroughly air-dried. The dry resin is treated with 10 mL of cleavage cocktail (trifluoroacetic acid:water:triisopropylsilane, 95:2.5:2.5 v/v) for 2 hours at room temperature. The resin is filtered off, washed twice each with 2 mL of neat TFA, and the combined filtrates are treated with 5-fold cold diethyl ether (−20° C.) to precipitate the crude peptide. The peptide/ether suspension is then centrifuged at 3500 rpm for 2 min to form a solid pellet, the supernatant is decanted, and the solid pellet is triturated with ether two additional times and dried in vacuo. The crude peptide is solubilized in 20% acetonitrile/20% acetic acid/60% water and purified by RP-HPLC on a Luna 5 μm Phenyl-Hexyl Preparative Column (21×250 mm, Phenomenex) with linear gradients of 100% acetonitrile and 0.1% TFA/water buffer system (30-50% acetonitrile in 60 min). The purity of peptide is assessed using analytical RP-HPLC and pooling criteria is >95%. The main pool purity of Example 1 is found to be 99.2%. Subsequent lyophilization of the final main product pool yields a lyophilized peptide TFA salt. The molecular weight is determined by LC-MS (obsd: M+4H+/4=1219.9; Calc M+4H+/4=1220.1).

EXAMPLE 2

Example 2 is a compound represented by the following description:

(SEQ ID NO: 7)
Y-Aib-QGT-αMeF-TSDYSI-αMeL-LDKK((2-[2-(2-amino-ethoxy)-ethoxy]-acetyl)$_2$-(γGlu)-CO—$(CH_2)_{18}$—$CO_2H$)AQ-Aib-AFIEYLLEGGPSSGAPPPS-$NH_2$.

Below is a depiction of the structure of Example 2 (SEQ ID NO:7) using the standard single letter amino acid codes with the exception of residues Aib2, αMeF6, αMeL13, K17 and Aib20, where the structures of these amino acid residues have been expanded:

Similar processes to those described above for Example 1 are used to synthesize the peptide backbone, to conjugate the fatty acid-linker moiety, to examine the purity, and to confirm the molecular weight of Example 2.

EXAMPLE 3

Example 3 is a compound represented by the following description:

(SEQ ID NO: 8)
Y-Aib-HGT-αMeF(2F)-TSDYSILLDKK((2-[2-(2-amino-ethoxy)-ethoxy]-acetyl)$_2$-(γGlu)-CO—$(CH_2)_{18}$—$CO_2H$)AQ-Aib-AFIEYLLEGGPSSGAPPPS-$NH_2$.

Below is a depiction of the structure of Example 3 (SEQ ID NO:8) using the standard single letter amino acid codes with the exception of residues Aib2, αMeF(2F)6, K17, and Aib20, where the structures of these amino acid residues have been expanded:

(SEQ ID NO: 7)

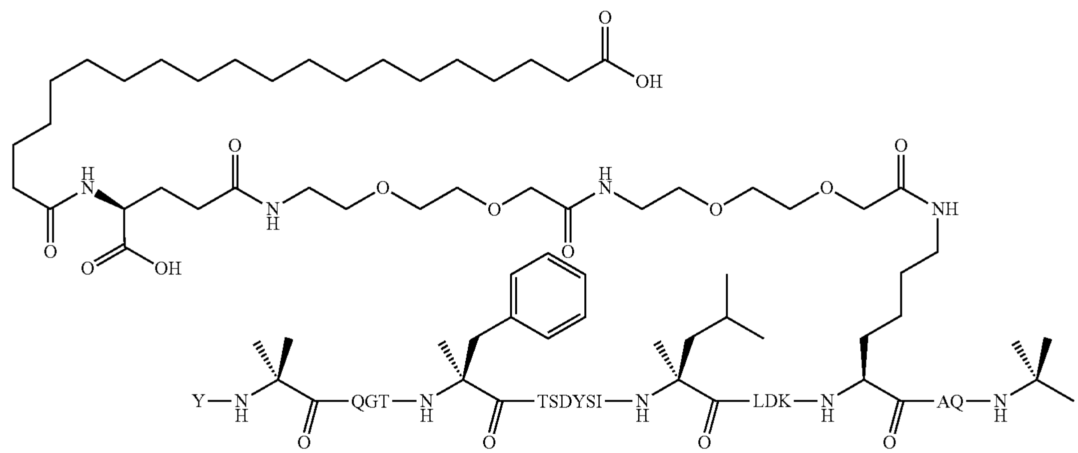

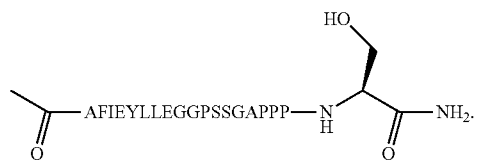

(SEQ ID NO: 8)

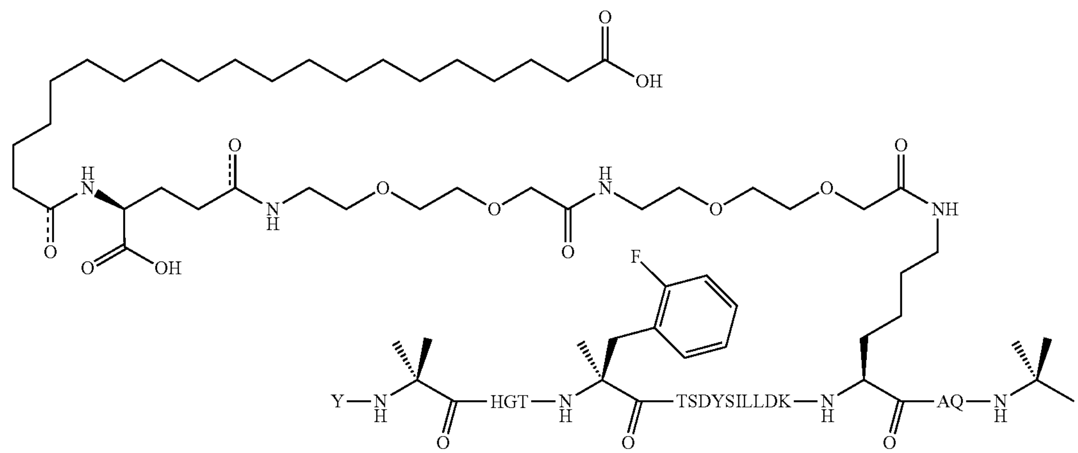

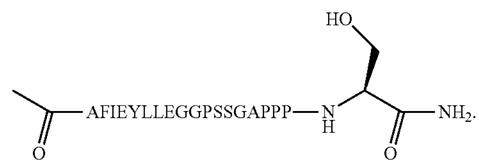

Similar processes to those described above for Example 1 are used to synthesize the peptide backbone, to conjugate the fatty acid-linker moiety, to examine the purity, and to confirm the molecular weight of Example 3.

EXAMPLE 4

Example 4 is a compound represented by the following description:

(SEQ ID NO: 9)
Y-Aib-QGT-αMeF(2F)-TSDYSILLDKK((2-[2-(2-amino-ethoxy)-ethoxy]-acetyl)-(γGlu)-CO-$(CH_2)_{18}$-$CO_2H$)AQ-Aib-AFIEYLLEGGPSSGAPPPS-$NH_2$.

Below is a depiction of the structure of Example 4 (SEQ ID NO:9) using the standard single letter amino acid codes with the exception of residues Aib2, αMeF(2F)6, K17, and Aib20, where the structures of these amino acid residues have been expanded:

(SEQ ID NO: 9)

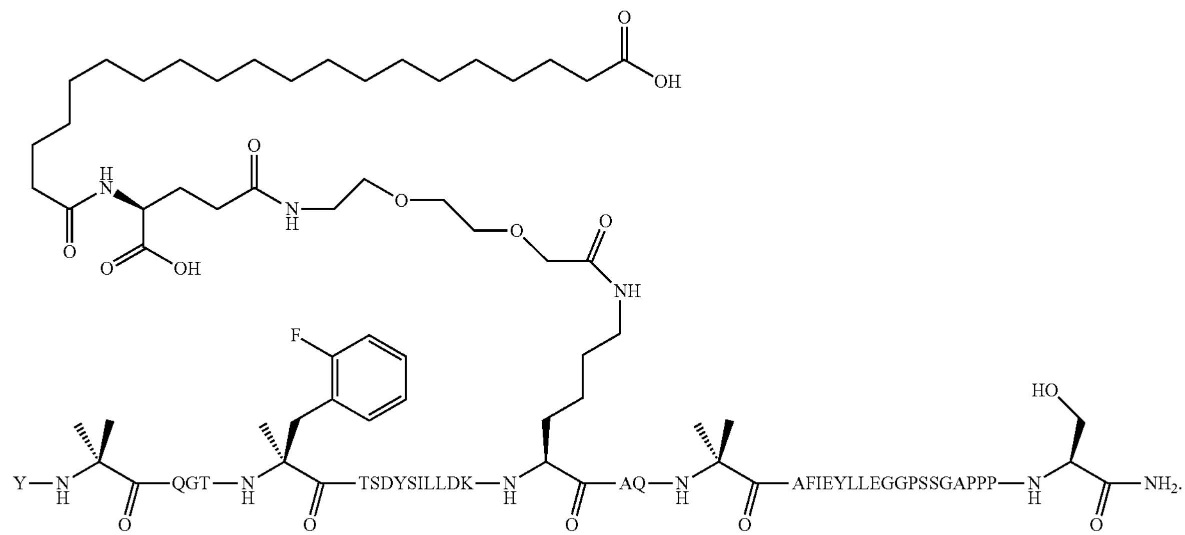

Similar processes to those described above for Example 1 are used to synthesize the peptide backbone, to conjugate the fatty acid-linker moiety, to examine the purity, and to confirm the molecular weight of Example 4.

EXAMPLE 5

Example 5 is a compound represented by the following description:

(SEQ ID NO: 10)
Y-Aib-QGT-αMeF(2F)-TSDYSILLDKK((2-[2-(2-amino-ethoxy)-ethoxy]-acetyl)-(γGlu)-CO—$(CH_2)_{18}$—$CO_2H$)AQQAFIEYLLEGGPSSGAPPPS-$NH_2$.

Below is a depiction of the structure of Example 5 (SEQ ID NO: 10) using the standard single letter amino acid codes with the exception of residues Aib2, αMeF(2F)6 and K17, where the structures of these amino acid residues have been expanded:

(SEQ ID NO: 10)

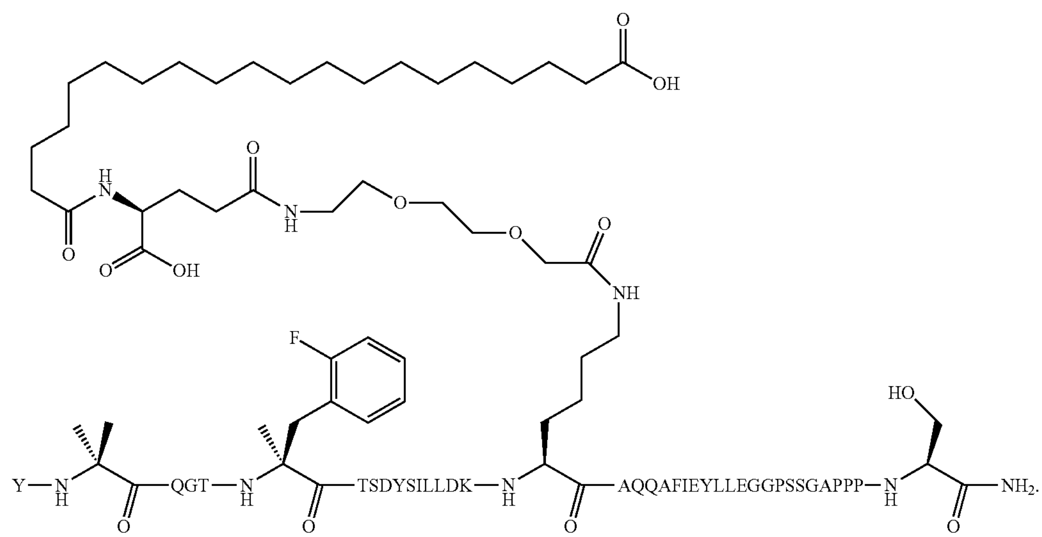

Similar processes to those described above for Example 1 are used to synthesize the peptide backbone, to conjugate the fatty acid-linker moiety, to examine the purity, and to confirm the molecular weight of Example 5.

EXAMPLE 6

Example 6 is a compound represented by the following description:

(SEQ ID NO: 11)
Y-Aib-QGT-αMeF(2F)-TSDYSILLDKK((2-[2-(2-amino-ethoxy)-ethoxy]-acetyl)-(γGlu)-CO—$(CH_2)_{18}$—$CO_2H$)AQHAFIEYLLEGGPSSGAPPPS-$NH_2$.

Below is a depiction of the structure of Example 6 (SEQ ID NO:11) using the standard single letter amino acid codes with the exception of residues Aib2, αMeF(2F)6, and K17, where the structures of these amino acid residues have been expanded:

(SEQ ID NO: 11)

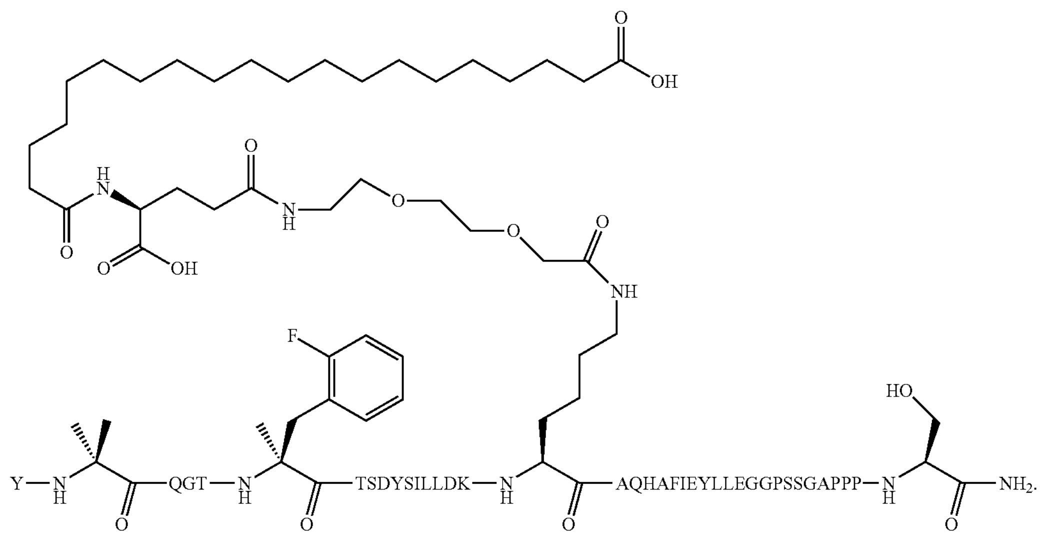

Similar processes to those described above for Example 1 are used to synthesize the peptide backbone, to conjugate the fatty acid-linker moiety, to examine the purity, and to confirm the molecular weight of Example 6.

In Vitro Function

Binding Affinity:

Radioligand competition binding assays are run to determine the equilibrium dissociation constant for Example compounds and comparator molecules. Such assay use scintillation proximity assay (SPA) methods and membranes prepared from transfected HEK293 cells overexpressing the human GIP receptor (GIPR), GLP-1 receptor (GLP-1R) or human glucagon receptor (GcgR).

The assays are performed in the presence of bacitracin as a non-specific blocking agent to prevent acylated moieties of test analogs from binding to protein components used in standard assay buffers (e.g., albumin).

Competition curves are plotted as the percent specific inhibition (y-axis) versus log concentration of compound (x-axis) and analyzed using a four parameter nonlinear regression fit with variable slope (ABase or Genedata). $K_i$ values are calculated according to the equation $K_i = IC_{50}/(1+(D/K_d))$, where $IC_{50}$ is the concentration of compound resulting in 50% inhibition of binding, D is the concentration of radioligand used in the assay, and $K_d$ is the equilibrium dissociation constant for the receptor and the radioligand, determined from saturation binding analysis (shown in Table 1 below).

TABLE 1

Equilibrium Dissociation Constants ($K_d$) Determined from Saturation Binding Analysis. $K_d$, nM

| GLP-1R | GcgR | GIPR |
|---|---|---|
| 1.2 | 3.9 | 0.14 |

$K_i$ values of exemplary analogs and comparator molecules are shown in Table 2.

TABLE 2

In Vitro Binding Affinity ($K_i$) of Examples and Comparators for Human GIPR, GLP-1R and GcgR.

| | $K_i$, nM (SEM, n) | | |
|---|---|---|---|
| Molecule | GcgR | GIPR | GLP-1R |
| hGcg | 3.1 (0.5, 4) | | |
| hGIP | | 0.12 (0.02, 4) | |
| hGLP-1 | | | 1.2 (0.2, 4) |
| Example 1 | 0.955 (0.182, 3) | 0.0278 (0.00297, 3) | 2.51 (0.930, 3) |
| Example 2 | 1.49 (0.201, 3) | 0.0413 (0.0129, 3) | 2.41 (se = 0.720, 3) |
| Example 3 | 0.469 (0.121, 5) | 0.0684 (0.0193, 5) | 1.66 (se = 0.950, 5) |
| Example 4 | 0.637 (0.0319, 3) | 0.0832 (0.0273, 3) | 1.21 (se = 0.0737, 3) |
| Example 5 | 0.419 (0.0430, 4) | 0.0347 (0.0112, 4) | 1.17 (se = 0.674, 4) |
| Example 6 | 0.382 (0.0587, 4) | 0.0388 (0.00813, 4) | 0.822 (se = 0.379, 4) |

NOTE:
A qualifier (>) indicates the data did not reach 50% inhibition relative to maximum binding, whereby the $K_i$ was calculated using the highest concentration tested in the assay.
n = 1/x means that only one value out of the total number of replicates (x) is used to express the mean.
SEM is only calculated when n = 2 or greater non-qualified results exist.

As seen in Table 2, exemplary analogs have binding affinity at each of the GIP, GLP-1 and Gcg receptors.

Functional Activity:

Functional activity is determined in GIP-R-GLP-1R- and GcgR-expressing HEK-293 clonal cell lines. Each receptor over-expressing cell line is treated with peptide (20 point CRC, 2.75-fold Labcyte Echo direct dilution) in DMEM (Gibco Cat #31053) supplemented with 1X GlutaMAX™ (Gibco Cat #35050), 0.25% FBS (Fetal Bovine Serum, Gibco Cat #26400), 0.05% fraction V BSA (Bovine Serum Albumin, Gibco Cat #15260), 250 µM IBMX and 20 mM HEPES (Gibco Cat #15630) in a 20 µl assay volume.

After a 60-minute incubation at room temperature, the resulting increase in intracellular cAMP is quantitatively determined using the CisBio cAMP Dynamic 2 HTRF Assay Kit (62AM4PEJ). Briefly, cAMP levels within the cell are detected by adding the cAMP-d2 conjugate in cell lysis buffer followed by the antibody anti-cAMP-$Eu^{3+}$-Cryptate, also in cell lysis buffer. The resulting competitive assay is incubated for at least 60 minutes at room temperature and then detected using a PerkinElmer Envision® Instrument with excitation at 320 nm and emission at 665 nm and 620 nm. Envision units (emission at 665 nm/620 nm*10,000) are inversely proportional to the amount of cAMP present and were converted to nM cAMP per well using a cAMP standard curve.

The amount of cAMP generated (nM) in each well is converted to a percent of the maximal response observed with either human GLP-1(7-36)$NH_2$, human Gcg, or human GIP(1-42)$NH_2$. A relative $EC_{50}$ value is derived by non-linear regression analysis using the percent maximal response vs. the concentration of peptide added, fitted to a four-parameter logistic equation.

Data for exemplary analogs and hGIP(1-42)$NH_2$, hGLP-1(7-36)$NH_2$ and hGcg are shown in Table 3 below.

TABLE 3

Functional cAMP Potency ($EC_{50}$) for Exemplary Analogs and Comparators in the Presence of FBS and BSA.

| | cAMP $EC_{50}$, nM (SEM, n) | | |
|---|---|---|---|
| | GcgR | GIPR | GLP-1R |
| hGcg | 0.0114 (0.0014, 12) | | |
| gGIP amide | | 0.0979 (0.0088, 12) | |
| hGLP-1 amide | | | 0.0424 (0.0043, 12) |
| Example 1 | 6.33 (0.905, 3) | 1.82 (0.332, 3) | 12.6 (1.42, 3) |
| Example 2 | 4.75 (0.827, 3) | 1.34 (0.216, 3) | 11.6 (2.26, 3) |
| Example 3 | 3.46 (0.835, 7) | 1.37 (0.518, 7) | 13.1 (3.06, 7) |
| Example 4 | 1.78 (0.400, 5) | 1.37 (0.422, 5) | 10.6 (3.29, 5) |
| Example 5 | 1.87 (0.254, 5) | 1.91 (0.618, 5) | 13.0 (2.59, 5) |
| Example 6 | 1.76 (0.218, 4) | 1.41 (0.363, 4) | 8.94 (2.76, 4) |

NOTE:
$EC_{50}$ determination of human GLP-1(7-36)$NH_2$ at human GLP-1R, human Gcg at human GcgR, and human GIP(1-42)$NH_2$ at human GIP-R: the peptide concentration ranges were 448 pM to 99.5 nM.
$EC_{50}$ determination of Examples at human GLP-1R, human GcgR, and human GIP-R: the peptide concentration ranges were 51.5 fM to 11.4 μM.

As seen in Table 3, in the presence of FBS and BSA, exemplary analogs have agonist activities as determined by human GIP-R, GLP-1R, and GcgR cAMP assays, which are lower than the native ligands.

An additional set of cAMP assays are conducted in HEK293 cells expressing the human GLP-1, GIP and glucagon receptors. Using homogeneous time resolved fluorescence methods, assays are conducted to determine the intrinsic potency of exemplary analogs and comparator molecules performed in the presence of casein (instead of serum albumin) as a nonspecific blocker, which does not interact with the fatty acid moieties of the analyzed molecules.

Intracellular cAMP levels are determined by extrapolation using a standard curve. Dose response curves of compounds are plotted as the percentage of stimulation normalized to minimum (buffer only) and maximum (maximum concentration of each control ligand) values and analyzed using a four parameter non-linear regression fit with a variable slope (Genedata Screener 13). $EC_{50}$ is the concentration of compound causing half-maximal simulation in a dose response curve.

Data are provided below in Table 4.

TABLE 4

Functional Activation of hGLP-1R, hGIPR, hGcgR in the Presence of 0.1% Casein.

| | cAMP $EC_{50}$, nM (SEM, n) | | |
|---|---|---|---|
| | GcGR | GIPR | GLP-1R |
| hGcg | 0.0119 (0.00356, 163) | | |
| hGIP amide | | 0.154 (0.037, 118) | |
| gGLP-1 amide | | | 0.063 (0.022, 197) |
| Example 1 | 0.158 (0.0464, 6) | 0.0226 (0.00787, 5) | 0.112 (0.0250, 5) |
| Example 2 | 0.0960 (0.0295, 7) | 0.0329 (0.0136, 7) | 0.106 (0.0155, 7) |
| Example 3 | 0.0301 (0.00811, 5) | 0.0215 (0.00338, 4) | 0.104 (0.0300, 4) |
| Example 4 | 0.0296 (0.00628, 5) | 0.0321 (0.0110, 4) | 0.145 (0.0309, 4) |
| Example 5 | 0.0343 (0.00555, 4) | 0.0306 (0.00998, 5) | 0.103 (0.0263, 4) |
| Example 6 | 0.0293 (0.00562, 4) | 0.0349 (0.00643, 4) | 0.115 (0.0305, 4) |

As seen in Table 4, exemplary analogs stimulate cAMP from human GIP, GLP-1 and glucagon receptors in the presence of 0.1% casein.

SEQ ID NO: 1 - Human glucagon
HSQGTFTSDYSKYLDSRRAQDFVQWLMNT

SEQ ID NO: 2 - Human GLP-1 (7-36) amide
HAEGTFTSDVSSYLEGQAAKEFIAWLVKGR-$NH_2$

SEQ ID NO: 3 - Human OXM
HSQGTFTSDYSKYLDSRRAQDFVQWLMNTKRNRNNIA

SEQ ID NO: 4 - Human GIP
YAEGTFISDYSIAMDKIHQQDFVNWLLAQKGKKNDWKHNITQ

SEQ ID NO: 5 - Incretin analog
$YX_2X_3GTX_6TSDYSIX_{13}LDKX_{17}AQX_{20}AFIEYLLEGGPSSGAPPPS$
where $X_2$ is Aib;

$X_3$ is Q or H;

$X_6$ is αMeF or αMeF(2F);

$X_{13}$ is L or αMeL;

$X_{17}$ is any amino acid with a functional group available for conjugation, where the functional group is conjugated to a $C_{16}$-$C_{22}$ fatty acid;

$X_{20}$ is Aib, Q or H

-continued

SEQ ID NO: 6 - Incretin analog
Y-Aib-QGT-αMeF-TSDYSILLDKK((2-[2-(2-amino-ethoxy)-ethoxy]-acetyl)$_2$-(γGlu)-

CO—$(CH_2)_{18}$—$CO_2$H)AQ-Aib-AFIEYLLEGGPSSGAPPPS-$NH_2$

SEQ ID NO: 7 - Incretin analog
Y-Aib-QGT-αMeF-TSDYSI-αMeL-LDKK((2-[2-(2-amino-ethoxy)-ethoxy]-acetyl)$_2$-

(γGlu)-CO—$(CH_2)_{18}$—$CO_2$H)AQ-Aib-AFIEYLLEGGPSSGAPPPS-$NH_2$

SEQ ID NO: 8 - Incretin analog
Y-Aib-HGT-αMeF(2F)-TSDYSILLDKK((2-[2-(2-amino-ethoxy)-ethoxy]-acetyl)$_2$-

(γGlu)-CO—$(CH_2)_{18}$—$CO_2$H)AQ-Aib-AFIEYLLEGGPSSGAPPPS-$NH_2$

SEQ ID NO: 9 - Incretin analog
Y-Aib-QGT-αMeF(2F)-TSDYSILLDKK((2-[2-(2-amino-ethoxy)-ethoxy]-acetyl)-(γGlu)-

CO—$(CH_2)_{18}$—$CO_2$H)AQ-Aib-AFIEYLLEGGPSSGAPPPS-$NH_2$

SEQ ID NO: 10 - Incretin analog
Y-Aib-QGT-αMeF(2F)-TSDYSILLDKK((2-[2-(2-amino-ethoxy)-ethoxy]-acetyl)-(γGlu)-

CO—$(CH_2)_{18}$—$CO_2$H)AQQAFIEYLLEGGPSSGAPPPS-$NH_2$

SEQ ID NO: 11 - Incretin analog
Y-Aib-QGT-αMeF(2F)-TSDYSILLDKK((2-[2-(2-amino-ethoxy)-ethoxy]-acetyl)-(γGlu)-

CO—$(CH_2)_{18}$—$CO_2$H)AQHAFIEYLLEGGPSSGAPPPS-$NH_2$

SEQ ID NO: 12 - Artificial sequence
GPSSGAPPPS

---

The invention claimed is:

1. An incretin analog comprising:

$YX_2X_3GTX_6TSDYSIX_{13}LDKX_{17}AQX_{20}AFIEYLLEGGPSSGAPPPS$, wherein:

$X_2$ is Aib, $X_3$ is Q or H, $X_6$ is αMeF or αMeF(2F), $X_{13}$ is L or αMeL, $X_{17}$ is any amino acid with a functional group available for conjugation, and the functional group is conjugated to a $C_{16}$-$C_{22}$ fatty acid, $X_{20}$ is Aib, Q or H, (SEQ ID NO:5), and the C-terminal amino acid is optionally amidated;

or a pharmaceutically acceptable salt thereof.

2. The incretin analog of claim 1, wherein the amino acid with a functional group available for conjugation at position $X_{17}$ is selected from the group consisting of K, C, E and D.

3. The incretin analog of claim 1, wherein the amino acid with a functional group available for conjugation at position $X_{17}$ is K.

4. The incretin analog of claim 1, wherein the amino acid with the functional group available for conjugation at position $X_{17}$ and the $C_{16}$-$C_{22}$ fatty acid are conjugated by a linker between the amino acid and the fatty acid.

5. The incretin analog of claim 4, wherein the linker comprises one to four amino acids.

6. The incretin analog of claim 5, wherein the amino acids are Glu or γGlu.

7. The incretin analog of claim 4, wherein the linker further comprises the following structure:

$H—\{NH—CH_2—CH_2—[O—CH_2—CH_2]_m—O—(CH_2)_p—CO\}_n—OH$, wherein m is any integer from 1 to 12, n is any integer from 1 to 12, and p is 1 or 2.

8. The incretin analog of claim 4, wherein the linker further comprises one to four (2-[2-(2-amino-ethoxy)-ethoxy]-acetyl) moieties.

9. The incretin analog of claim 1, wherein $X_{17}$ is K chemically modified through conjugation to an epsilon-amino group of a K side-chain with the following structure:

$(2\text{-}[2\text{-}(2\text{-amino-ethoxy})\text{-ethoxy}]\text{-acetyl})_a\text{-}(\gamma Glu)_b\text{-}CO—(CH_2)_c—CO_2H$, wherein $_a$ is 0, 1 or 2; $_b$ is 1 or 2; and $_c$ is an integer between 16 to 18.

10. The incretin analog of claim 9, wherein a is 1.

11. The incretin analog of claim 9, wherein a is 2.

12. The incretin analog of claim 9, wherein b is 1.

13. The incretin analog of claim 9, wherein b is 2.

14. The incretin analog of claim 9, wherein c is 18.

15. The incretin analog of claim 1, wherein $X_{13}$ is αMeL.

16. The incretin analog of claim 1, wherein $X_{13}$ is L.

17. The incretin analog of claim 1, wherein $X_3$ is Q.

18. The incretin analog of claim 1, wherein $X_6$ is αMeF.

19. The incretin analog of claim 1, wherein $X_6$ is αMeF (2F).

20. An incretin analog having a formula selected from the group consisting of SEQ ID NOS:5-7 and 9-11.

21. A method of treating a disease selected from the group consisting of diabetes mellitus, obesity, fatty liver disease, non-alcoholic steatohepatitis, dyslipidemia and metabolic syndrome, the method comprising the step of:

administering to an individual in need thereof an effective amount of an incretin analog of claim 1.

22. A method of treating type II diabetes mellitus, the method comprising the step of:

administering to an individual in need thereof an effective amount of an incretin analog of claim 1.

23. A pharmaceutical composition comprising:

an incretin analog of claim 1; and a pharmaceutically acceptable carrier, diluent, or excipient.

* * * * *

SEQUENCE LISTING

```
Sequence total quantity: 12
SEQ ID NO: 1            moltype = AA  length = 29
FEATURE                 Location/Qualifiers
source                  1..29
                        mol_type = protein
                        organism = Homo sapiens
SEQUENCE: 1
HSQGTFTSDY SKYLDSRRAQ DFVQWLMNT                                    29

SEQ ID NO: 2            moltype = AA  length = 30
FEATURE                 Location/Qualifiers
source                  1..30
                        mol_type = protein
                        organism = Homo sapiens
SEQUENCE: 2
HAEGTFTSDV SSYLEGQAAK EFIAWLVKGR                                   30

SEQ ID NO: 3            moltype = AA  length = 37
FEATURE                 Location/Qualifiers
source                  1..37
                        mol_type = protein
                        organism = Homo sapiens
SEQUENCE: 3
HSQGTFTSDY SKYLDSRRAQ DFVQWLMNTK RNRNNIA                           37

SEQ ID NO: 4            moltype = AA  length = 42
FEATURE                 Location/Qualifiers
source                  1..42
                        mol_type = protein
                        organism = Homo sapiens
SEQUENCE: 4
YAEGTFISDY SIAMDKIHQQ DFVNWLLAQK GKKNDWKHNI TQ                     42

SEQ ID NO: 5            moltype = AA  length = 39
FEATURE                 Location/Qualifiers
REGION                  1..39
                        note = Synthetic Construct
SITE                    2
                        note = X at position 2 is Aib
SITE                    3
                        note = X at position 3 is Gln or His
```

-continued

```
SITE                    6
                        note = X at position 6 is alpha-methyl-phenylalanine or
                         alpha-methyl-2-fluorophenylalanine
SITE                    13
                        note = X at position 13 is alpha-methyl-Leu or Leu
MOD_RES                 17
                        note = X at position 17 is any amino acid with a functional
                         group available for conjugation wherein the functional
                         group is conjugated to a C16-C22 fatty acid
SITE                    20
                        note = X at position 2 is Aib, Gln, or His
source                  1..39
                        mol_type = protein
                        organism = synthetic construct
SEQUENCE: 5
YXXGTXTSDY SIXLDKXAQX AFIEYLLEGG PSSGAPPPS                          39

SEQ ID NO: 6            moltype = AA  length = 39
FEATURE                 Location/Qualifiers
REGION                  1..39
                        note = Synthetic Construct
SITE                    2
                        note = X at position 2 is alpha-amino-isobutyric acid
SITE                    6
                        note = X at position 6 is alpha-methyl-phenylalanine
MOD_RES                 17
                        note = Lys at position 17 is chemically modified by
                         conjugation of the epsilon-amino group of the Lys side
                         chain with
                         (2-[2-(2-Amino-ethoxy)-ethoxy]-acetyl)2-(gamma-Glu)-CO-(CH2
                         )18-CO2H
SITE                    20
                        note = X at position 20 is alpha-amino-isobutyric acid
MOD_RES                 39
                        note = Ser at position 39 is optionally amidated
source                  1..39
                        mol_type = protein
                        organism = synthetic construct
SEQUENCE: 6
YXQGTXTSDY SILLDKKAQX AFIEYLLEGG PSSGAPPPS                          39

SEQ ID NO: 7            moltype = AA  length = 39
FEATURE                 Location/Qualifiers
REGION                  1..39
                        note = Synthetic Construct
SITE                    2
                        note = X at position 2 is alpha-amino-isobutyric acid
SITE                    6
                        note = X at position 6 is alpha-methyl-phenylalanine
SITE                    13
                        note = X at position 13 is alpha-methyl-Leu
MOD_RES                 17
                        note = Lys at position 17 is chemically modified by
                         conjugation of the epsilon-amino group of the Lys side
                         chain with
                         (2-[2-(2-Amino-ethoxy)-ethoxy]-acetyl)2-(gamma-Glu)-CO-(CH2
                         )18-HCO2H
SITE                    20
                        note = X at position 2 is alpha-amino-isobutyric acid
MOD_RES                 39
                        note = Ser at position 39 is optionally amidated
source                  1..39
                        mol_type = protein
                        organism = synthetic construct
SEQUENCE: 7
YXQGTXTSDY SIXLDKKAQX AFIEYLLEGG PSSGAPPPS                          39

SEQ ID NO: 8            moltype = AA  length = 39
FEATURE                 Location/Qualifiers
REGION                  1..39
                        note = Synthetic Construct
SITE                    2
                        note = X at position 2 is alpha-amino-isobutyric acid
SITE                    6
                        note = X at position 6 is alpha-methyl-2-fluorophenylalanine
MOD_RES                 17
                        note = Lys at position 17 is chemically modified by
                         conjugation of the epsilon-amino group of the Lys side
                         chain with
```

-continued

```
                       (2-[2-(2-Amino-ethoxy)-ethoxy]-acetyl)2-(gamma-Glu)-CO-(CH2
                       )18-CO2H
SITE                   20
                       note = X at position 20 is alpha-amino-isobutyric acid
MOD_RES                39
                       note = Ser at position 39 is optionally amidated
source                 1..39
                       mol_type = protein
                       organism = synthetic construct
SEQUENCE: 8
YXHGTXTSDY SILLDKKAQX AFIEYLLEGG PSSGAPPPS                          39

SEQ ID NO: 9           moltype = AA  length = 39
FEATURE                Location/Qualifiers
REGION                 1..39
                       note = Synthetic Construct
SITE                   2
                       note = X at position 2 is alpha-amino-isobutyric acid
SITE                   6
                       note = X at position 6 is alpha-methyl-2-fluorophenylalanine
MOD_RES                17
                       note = Lys at position 17 is chemically modified by
                        conjugation of the epsilon-amino group of the Lys side
                        chain with
                        (2-[2-(2-Amino-ethoxy)-ethoxy]-acetyl)-(gamma-Glu)-CO-(CH2)
                        18-CO2H
SITE                   20
                       note = X at position 20 is alpha-amino-isobutyric acid
MOD_RES                39
                       note = Ser at position 39 is optionally amidated
source                 1..39
                       mol_type = protein
                       organism = synthetic construct
SEQUENCE: 9
YXQGTXTSDY SILLDKKAQX AFIEYLLEGG PSSGAPPPS                          39

SEQ ID NO: 10          moltype = AA  length = 39
FEATURE                Location/Qualifiers
REGION                 1..39
                       note = Synthetic Construct
SITE                   2
                       note = X at position 2 is alpha-amino-isobutyric acid
SITE                   6
                       note = X at position 6 is alpha-methyl-2-fluorophenylalanine
MOD_RES                17
                       note = Lys at position 17 is chemically modified by
                        conjugation of the epsilon-amino group of the Lys side
                        chain with
                        (2-[2-(2-Amino-ethoxy)-ethoxy]-acetyl)-(gamma-Glu)-CO-(CH2)
                        18-CO2H
MOD_RES                39
                       note = Ser at position 39 is optionally amidated
source                 1..39
                       mol_type = protein
                       organism = synthetic construct
SEQUENCE: 10
YXQGTXTSDY SILLDKKAQQ AFIEYLLEGG PSSGAPPPS                          39

SEQ ID NO: 11          moltype = AA  length = 39
FEATURE                Location/Qualifiers
REGION                 1..39
                       note = Synthetic Construct
SITE                   2
                       note = X at position 2 is alpha-amino-isobutyric acid
SITE                   6
                       note = X at position 6 is alpha-methyl-2-fluorophenylalanine
MOD_RES                17
                       note = Lys at position 17 is chemically modified by
                        conjugation of the epsilon-amino group of the Lys side
                        chain with
                        (2-[2-(2-Amino-ethoxy)-ethoxy]-acetyl)-(gamma-Glu)-CO-(CH2)
                        18-CO2H
MOD_RES                39
                       note = Ser at position 39 is optionally amidated
source                 1..39
                       mol_type = protein
                       organism = synthetic construct
SEQUENCE: 11
YXQGTXTSDY SILLDKKAQH AFIEYLLEGG PSSGAPPPS                          39
```

-continued

```
SEQ ID NO: 12           moltype = AA  length = 10
FEATURE                 Location/Qualifiers
REGION                  1..10
                        note = Synthetic Construct
source                  1..10
                        mol_type = protein
                        organism = synthetic construct
SEQUENCE: 12
GPSSGAPPPS                                                         10
```